(12) United States Patent
Webb et al.

(10) Patent No.: US 7,060,031 B2
(45) Date of Patent: Jun. 13, 2006

(54) METHOD AND APPARATUS FOR REMOTELY PROGRAMMING IMPLANTABLE MEDICAL DEVICES

(75) Inventors: James D Webb, Maple Grove, MN (US); Chester G. Nelson, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 5 days.

(21) Appl. No.: 10/072,782

(22) Filed: Feb. 8, 2002

(65) Prior Publication Data

US 2002/0123673 A1 Sep. 5, 2002

Related U.S. Application Data

(63) Continuation-in-part of application No. 09/466,284, filed on Dec. 17, 1999, now Pat. No. 6,497,655.

(51) Int. Cl.
*A61B 5/00* (2006.01)

(52) U.S. Cl. .......................................... 600/300; 607/2

(58) Field of Classification Search ........ 600/300–301; 607/30–31, 32, 60; 128/877–899, 920–925; 604/890.1–892.1; 705/2, 3; 709/217–219, 709/227–237
See application file for complete search history.

(56) References Cited

U.S. PATENT DOCUMENTS

| | | | |
|---|---|---|---|
| 4,140,131 A | 2/1979 | Dutcher et al. | |
| 4,295,474 A | 10/1981 | Fischell | |
| 4,494,950 A | 1/1985 | Fischell | |
| 4,842,531 A | 6/1989 | Takemura | |
| 4,886,064 A | 12/1989 | Strandberg | |
| 4,987,897 A | 1/1991 | Funke | |
| 5,076,272 A | 12/1991 | Ferek-Petric | |
| 5,321,618 A | 6/1994 | Gessman | |
| 5,345,362 A | 9/1994 | Winkler | |
| 5,371,692 A * | 12/1994 | Draeger et al. ............. | 702/122 |
| 5,434,611 A | 7/1995 | Tamura | |
| 5,441,047 A | 8/1995 | David et al. | |
| 5,447,164 A | 9/1995 | Shaya et al. | |
| 5,517,405 A | 5/1996 | McAndrew et al. | |
| 5,553,609 A | 9/1996 | Chen et al. | |
| 5,590,057 A | 12/1996 | Fletcher et al. | |
| 5,593,426 A | 1/1997 | Morgan et al. | |
| 5,594,638 A | 1/1997 | Iliff | |
| 5,615,112 A | 3/1997 | Liu Sheng et al. | |

(Continued)

OTHER PUBLICATIONS

Anderson, et al., "The use of Transtelephone Interrogation in the Management of patients with Implantable Cardioverter Defibrillators," *ECC*, vol. 12, P2247, Abstracts, Suppl. (Aug. 1991).

(Continued)

*Primary Examiner*—Robert L. Nasser
*Assistant Examiner*—Patricia C. Mallari
(74) *Attorney, Agent, or Firm*—Girma Wolde-Michael; Daniel G. Chapik

(57) ABSTRACT

The present invention provides a method and apparatus for remotely programming implantable medical devices. The apparatus includes a server adapted to receive and store at least one request to modify the behavior of an implantable medical device provided by a programmer adapted to allow a clinician to create the at least one request at a first selected time. The apparatus further includes a monitor adapted to receive the requests from the server and transmit the requests to the implantable medical device at a second selected time and a bi-directional communications system adapted to couple the server and the monitor.

3 Claims, 13 Drawing Sheets

U.S. PATENT DOCUMENTS

| | | | |
|---|---|---|---|
| 5,619,991 A | | 4/1997 | Sloane |
| 5,660,176 A | | 8/1997 | Iliff |
| 5,660,183 A | | 8/1997 | Chiang et al. |
| 5,701,904 A | | 12/1997 | Simmons et al. |
| 5,704,366 A | | 1/1998 | Tacklind et al. |
| 5,711,297 A | | 1/1998 | Iliff |
| 5,713,938 A | | 2/1998 | Chiang et al. |
| 5,716,382 A | | 2/1998 | Snell |
| 5,716,384 A | | 2/1998 | Snell |
| 5,720,770 A | * | 2/1998 | Nappholz et al. ............. 607/30 |
| 5,722,999 A | | 3/1998 | Snell |
| 5,752,976 A | * | 5/1998 | Duffin et al. ................. 607/32 |
| 5,755,742 A | | 5/1998 | Schuelke et al. |
| 5,772,586 A | | 6/1998 | Heinonen et al. |
| 5,791,907 A | | 8/1998 | Ramshaw et al. |
| 5,810,747 A | | 9/1998 | Brudny et al. |
| 5,836,975 A | | 11/1998 | DeGroot |
| 5,840,020 A | | 11/1998 | Heinonen et al. |
| 6,047,325 A | * | 4/2000 | Jain et al. ................... 709/227 |
| 6,059,692 A | * | 5/2000 | Hickman ....................... 482/8 |
| 6,132,363 A | * | 10/2000 | Freed et al. ................... 600/16 |
| 6,168,563 B1 | * | 1/2001 | Brown ........................ 600/301 |
| 6,249,705 B1 | * | 6/2001 | Snell ........................... 607/59 |
| 6,250,309 B1 | * | 6/2001 | Krichen et al. ............. 128/899 |
| 6,292,698 B1 | | 9/2001 | Duffin et al. |
| 6,304,788 B1 | * | 10/2001 | Eady et al. ................... 700/86 |
| 6,308,102 B1 | * | 10/2001 | Sieracki et al. ............... 607/59 |
| 6,358,202 B1 | * | 3/2002 | Arent ......................... 600/300 |
| 6,363,282 B1 | | 3/2002 | Nichols et al. |
| 6,385,593 B1 | | 5/2002 | Linberg |
| 6,386,882 B1 | | 5/2002 | Linberg |
| 6,411,851 B1 | | 6/2002 | Winkler |
| 6,418,346 B1 | | 7/2002 | Nelson et al. |
| 6,440,068 B1 | * | 8/2002 | Brown et al. ............... 600/300 |
| 6,442,433 B1 | | 8/2002 | Linberg |
| 6,477,424 B1 | * | 11/2002 | Thompson et al. ........... 607/60 |
| 6,494,831 B1 | * | 12/2002 | Koritzinsky ................ 600/301 |
| 6,539,947 B1 | * | 4/2003 | Boies et al. ................. 600/510 |
| 6,602,469 B1 | * | 8/2003 | Maus et al. ................. 422/68.1 |
| 6,804,558 B1 | * | 10/2004 | Haller et al. .................. 607/30 |

OTHER PUBLICATIONS

Bai et al., "Design and Development of an Interactive Medical Teleconsultation System Over the World Wide Web," *IEEE*, vol. 2, No. 2, p. 74-79 (Jun. 1998).

Chronaki et al., "*WebOnCOLL*: Medical Collaboration in Regional Healthcare Networks," *IEEE*, vol. 1, No. 4, p. 1089-777 (Dec. 1997).

Hudson et al., "Structuring Medical Information for Computer-Assisted Decision Support," *IEEE*, 19th International conference—IEEE/EMBS, Chicago, IL, p. 953-956, (Oct. 30-Nov. 2, 1997).

Hutten et al., "Cardiac Telemonitoring by Integrating Pacemaker Telemetry Within Worldwide Data Communication Systems," Proceedings—19th International Conference—IEEE/EMBS, Chicago, IL, p. 974-976 (Oct. 30-Nov. 2, 1997).

Krishnan et al., "A MultiMedia-Based Medical Database Network System for Special Clinical Procedures in Healthcare Delivery," *IEEE*, 19th International Conference—IEEE/EMBS, Chicago, IL, p. 936-38 (Oct. 30-Nov. 2, 1997).

Schreier et al., "The Influence of Infectious Disease on Ventricular Evoked Responses from Heart Transplants," *IEEE*, 19th International Conference—IEEE/EMBS, Chicago, IL, p. 169-71 (Oct. 30-Nov. 2, 1997).

Schreier et al., "Cardiac Telemonitoring by Integrating Pacemaker Telemetry Within Worldwide data Communication Systems," *IEEE*, 19th International Conference—IEEE/EMBS, Chicago, IL, p. 974-76 (Oct. 30-Nov. 2, 1997).

Internet, , http://www.healtheon.com/tech/index.html, Healtheon Technology (1999).

Internet, Press Release, "The Next Generation in Healthcare Information Management," http://home.mcis.washington.edu/mcis/news/thormcis.html, Healtheon Technology (1998).

* cited by examiner

FIG. 1

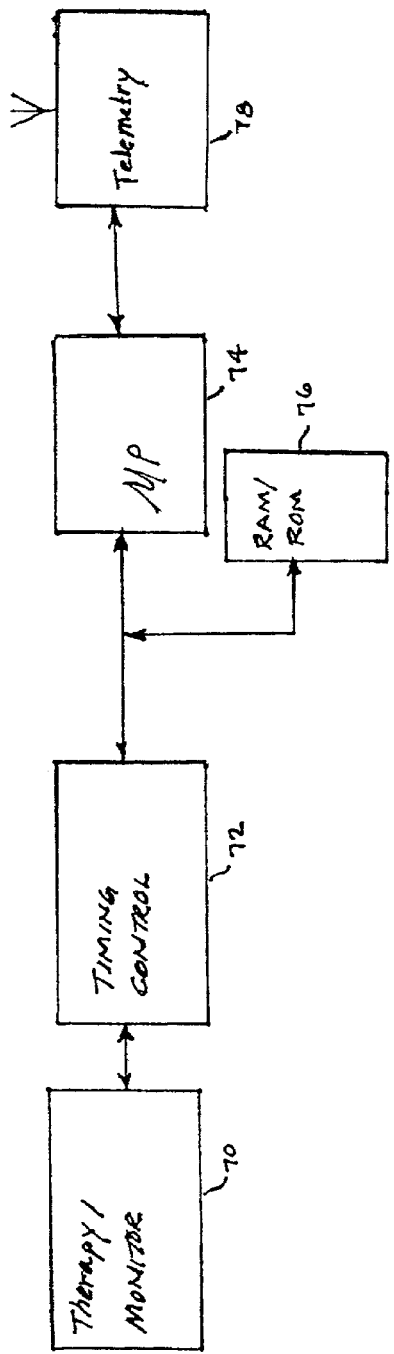
FIG. - 1
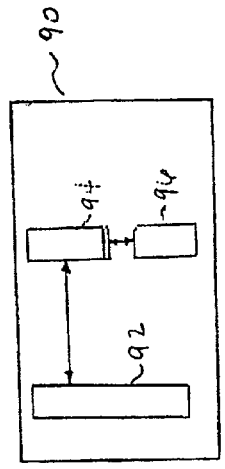
FIG. - 2
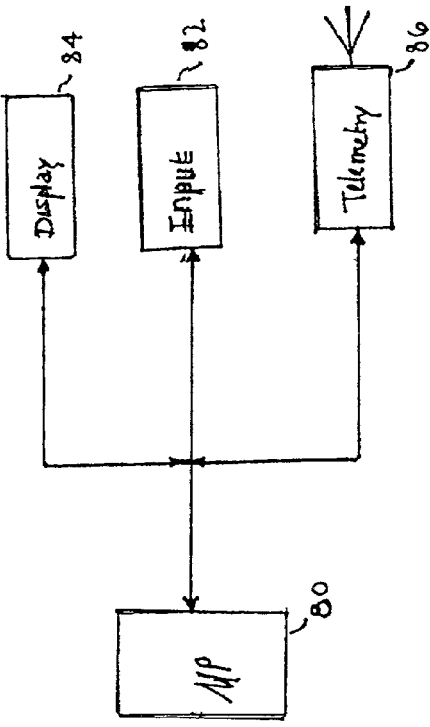
FIG. - 3A
FIG. - 3B

METHOD AND APPARATUS FOR REMOTELY PROGRAMMING IMPLANTABLE MEDICAL DEVICES

CROSS REFERENCE TO RELATED APPLICATIONS

This application is a continuation-in-part of U.S. patent application Ser. No. 09/466,284, filed on Dec. 17, 1999 now U.S. Pat. No. 6,497,655.

BACKGROUND OF THE INVENTION

1. Field of the Invention

This invention relates generally to implantable medical devices, and, more particularly, to remotely programming implantable medical devices.

2. Description of the Related Art

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide a seamless system of remote patient diagnostics, care and medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and temporaneous procedures relating to an IMD uplink with, for example, a programmer. It is required that the report contain the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the problems with the reporting procedures is the fact that it is error prone and requires rechecking of the data to verify accuracy.

Yet another condition of the prior art requires that a local and a remote clinician, as well as a patient in a clinic, all be present at the time that the IMD is programmed. Current practice dictates that the patient be accompanied by a clinician during programming operations. The patient and the accompanying clinician are generally required to have immediate access to rescue equipment, even for benign programming that poses little or no danger to the patient.

Yet a further condition of the prior art relates to the operator-programmer interface. Generally a medical device manager/technician, should be trained on the clinical and operational aspects of the programmer. Current practice requires that an operator attend a class/session sponsored by a clinic, hospital or the manufacturer to successfully manage a programmer-IMD procedure. Further, the manager should be able to keep abreast of new developments and new procedures in the management, maintenance and upgrade of the IMD. Accordingly, under current practice it is imperative that operators of programmers, IMDs and related medical devices be trained on a regular basis.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the IMDs including the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients world-wide.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29,1999, Ser. No. 09/429,956; "Apparatus and Method to Automate Remote Software Updates of Medical Device Systems," filed Oct. 29,1999, Ser. No. 09/429,960; "Method and Apparatus to Secure Data Transfer From Medical Device Systems," filed Nov. 2,1999, Ser. No. 09/431,881; "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 10,1999, Ser. No. 09/437,615; "Apparatus and Method for Remote Therapy and Diagnosis in Medical Devices Via Interface Systems," filed Dec. 14,1999, Ser. No. 09/460,580; which are all incorporated by reference herein in their entirety which are all incorporated by reference herein in their entirety, has become an important aspect of patient care. Thus, in light of the referenced disclosures, remote training of the technicians/operators of the programmers and other peripheral equipment, that are associated with the IMDs, is a vital step in providing efficient therapy and clinical care to the patient.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and /or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S. Pat. No. 4,494,950 issued Jan. 22, 1985. The disclosure relates to a system consisting of a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external programmer for telemetrically programming the modules.

Yet another example of remote monitoring of implanted cardioverter defibrillators is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer is remotely debugged, maintained, upgraded or modified to ultimately enhance the support it provides to the implantable device with which it is associated. Specifically, the Duffin et al disclosure is limited to notifying remote medical support personnel or an operator about impending problems with an IMD and also enables constant monitoring of the patient's position worldwide using the GPS system. However, Duffin et al does not teach the remote programming scheme contemplated by the present invention.

In a related art, Thompson discloses a patient tracking system in a copending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which an implantable medical device is remotely evaluated and monitored to effect functional and parametric tune up, upgrade and maintenance as needed.

Yet in another related art, Ferek-Petric discloses a system for communication with a medical device in a co-pending Ser. No. 09/348,506 which is incorporated by reference herein in its entirety. The disclosure relates to a system that enables remote communications with a medical device, such as a programmer. Particularly, the system enables remote communications to inform device experts about programmer status and problems. The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek-Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely. exercised. Further, because of the early warning or advance knowledge of the problem, the remote expert would be well informed to provide remote advice or guidance to service personnel or operators at the programmer.

While Ferek-Petric's invention advances the art in communications systems relating to interacting with a programmer via a communication medium such as the Internet, the system does neither propose nor suggest remote programming, debugging and maintenance of a programmer without the intervention of a service person.

Another disclosure relating to ambulatory patient health monitoring techniques utilizing interactive visual communications is disclosed by Daniel et al in U.S. Pat. No. 5,441,047, issued Aug. 15, 1995. The invention relates to a system in which the patient is monitored by a health care worker at a certain station, while the patient is at a remote location. The patient's condition is monitored in the home using various monitoring devices. The health care worker is placed into interactive visual communication with the patient.

Yet another prior art provides a monitoring method and a monitoring equipment in U.S. Pat. No. 5,840,020 by Pekka et al issued on Nov. 24, 1998. The patent relates to a monitoring equipment including means for receiving a measurement result indicating the patient's blood glucose level, and for storing it in memory. In order to improve and facilitate the treatment of the patient, the monitoring equipment further includes means for receiving data concerning the patient's diet, medication and physical strain and for storing it in the memory. A series of calculations are refined to provide predictive values Further, another prior art provides a method for monitoring the health of a patient as disclosed in U.S. Pat. No. 5,772,586 issued to Pekka et al on Jun. 30, 1998. The disclosure relates to a method for monitoring the health of a patient by utilizing measurements. In order to improve the contact between the patient and the person treating him, the results of the measurements are supplied via a communications device utilizing a wireless data transmission link to a data processing system available to the person monitoring the patient's health. The patient's health is monitored by means of the data stored in the data processing system.

Yet a further example of a prior art is provided in U.S. Pat. No. 5,701,904 by Simmons et al issued on Dec. 30, 1997 relating to telemedicine instrumentation pack. The invention includes a portable medical diagnostic apparatus for data gathering . A video camera generates signals based on images taken from the visual instruments. Other electronics circuitry generates signals based on output of the audio instrument and data-gathering instruments. The signals are transmitted to a remote site for analysis by medical personnel.

A related prior art is disclosed in U.S. Pat. No. 5,434,611 issued to Tamura on Jul. 18, 1995. The disclosure relates to a health care system which employs a two-way communications antenna television network to permit communication between a doctor and patients at different locations. The system utilizes a community antenna television (CATV) so that the doctor can directly interrogate patients at home, and the patients can be automatically monitored at home using images and voice by the doctor in the medical office, without hindrance to normal CATV broadcasting.

Yet another related prior art is disclosed in U.S. Pat. No. 5,791,907 by Ramshaw issued on Aug. 11, 1998. The disclosure relates to an interactive medical training device including a computer system with a display. The computer is programmed to provide education and training in medical procedures.

Another related prior art is disclosed in U.S. Pat. No. 5,810,747 by Brudny et al. issued on Sep. 22, 1998. The invention relates to an interactive intervention training system used for monitoring a patient. An expert system and a neural network determine a goal to be achieved during training.

One of the limitations of Brudny's teachings is the fact that the interactive training does not provide for a programmer type interface between the expert system (remote station) and a plurality of IMDs. Further, there is no software structure or scheme to provide the various remote programming functions contemplated by the present invention.

Some of the limitations of Ramshaw's disclosure, in light of the present invention, include the fact that there is no teaching of a program that is used for managing implantable devices to effect various clinical procedures and therapy based on a remotely transmitted interactive software from a web-based data center.

Further U.S. Pat. No. 5,590,057 by Ruuska et al., issued on Dec. 31, 1996 provides a training and certification system for a user to perform a task. The invention includes an input device, output device and a controller. The controller receives input data from the input device and controls the output displayed on the output device. The system presents a user with a pretest, a module containing instructions, information about a certain portion of the task to be performed, as well as mini-simulations and a variety of questions. The system presents a post-test result and determines if the user is certifiable.

Ruuska et al's disclosure relates to training on a task and provides an advance in computer implemented system for training and certifying a trainee to perform a task. However, in light of the present invention, Ruuska et al. has several limitations. Specifically, Ruuska does not disclose a programmer for managing the operations of IMDs. Further, Ruuska does not relate to a highly globally distributed number of programmers on which technicians need to be trained to operate both the programmers and the IMDs. In the present invention, each programmer may manage a plurality of IMDs via, preferably, a telemetric data transmission system. IMD data download, new software installation, patient history, including significant clinical/therapy information are routinely exchanged between the programmer and the IMDs using the program modules implemented by the present invention. The globally distributed programmers that manage the IMDs locally are connected, via a bi-directional communications link, to a remote data center to exchange data, voice and video. The remote data center is a universal command/control point in which expert system's reside.

Accordingly, it would be advantageous to provide a system in which a programmer could uplink to a remote expert data center to import enabling software for self-diagnosis, maintenance and upgrade of the programmer. Yet another desirable advantage would be to provide a system to implement the use of remote expert systems to manage a programmer on a real-time basis. A further desirable advantage would be to provide a communications scheme that is compatible with various communications media, to promote a fast uplink of a programmer to remote expert systems and specialized data resources. Yet a further desirable advantage would be to provide a communications scheme that would permit programming operations to be stored in a central repository before being transmitted to the patient. Yet another desirable advantage would be to provide a high speed communications scheme to enable the transmission of high fidelity sound, video and data to advance and implement efficient remote data management of a clinical/therapy system via a programmer or an interface medical device thereby enhancing patient clinical care. Preferably, a remote web-based expert data center would direct, command and control the clinical, therapeutic and operational functions of a multiple set of implantable medical devices, on a continuous and real time basis, utilizing a high speed communication scheme. As discussed herein below, the present invention provides these and other desirable advantages.

SUMMARY OF THE INVENTION

In one aspect of the instant invention, an apparatus is provided for remotely programming implantable medical devices. The apparatus includes a server adapted to receive and store at least one request to modify the behavior of an implantable medical device provided by a programmer adapted to allow a clinician to create the at least one request at a first selected time. The apparatus further includes a monitor adapted to receive the requests from the server and transmit the requests to the implantable medical device at a second selected time and a bi-directional communications system adapted to couple the server and the monitor.

In one aspect of the present invention, a method is provided for remotely programming implantable medical devices. The method includes programming at a first selected time at least one request to modify the operation of an implantable medical device and storing the request at a first selected location. The method further includes transmitting the request from the first selected location at a second selected time to a second selected location and transmitting the request from the second selected location to the implantable medical device.

BRIEF DESCRIPTION OF THE DRAWINGS

The invention may be understood by reference to the following description taken in conjunction with the accompanying drawings, in which like reference numerals identify like elements, and in which:

FIG. 1 shows a simplified schematic diagram of a system of major uplink and downlink telemetry communications that may couple a remote clinical station, a programmer and a plurality of implantable medical devices (IMDs), in accordance with one embodiment of the present invention;

FIG. 2 depicts a block diagram representing the major components of an IMD that may be used in the telemetry communications system illustrated in FIG. 1, in accordance with one embodiment of the present invention;

FIG. 3A shows a block diagram representing the major components of a programmer or interface medical device that may be used in the system illustrated in FIG. 1, in accordance with one embodiment of the present invention;

FIG. 3B shows a block diagram representing a laser transceiver for high speed transmission of voice, video and other data that may be used in the system shown in FIG. 1, in accordance with one embodiment of the present invention;

FIGS. 8A and 8B represent high level software logic for implementing a prescriptive or therapy related program in the wireless communication system shown in FIG. 4, in accordance with one embodiment of the present invention;

Figure 4:
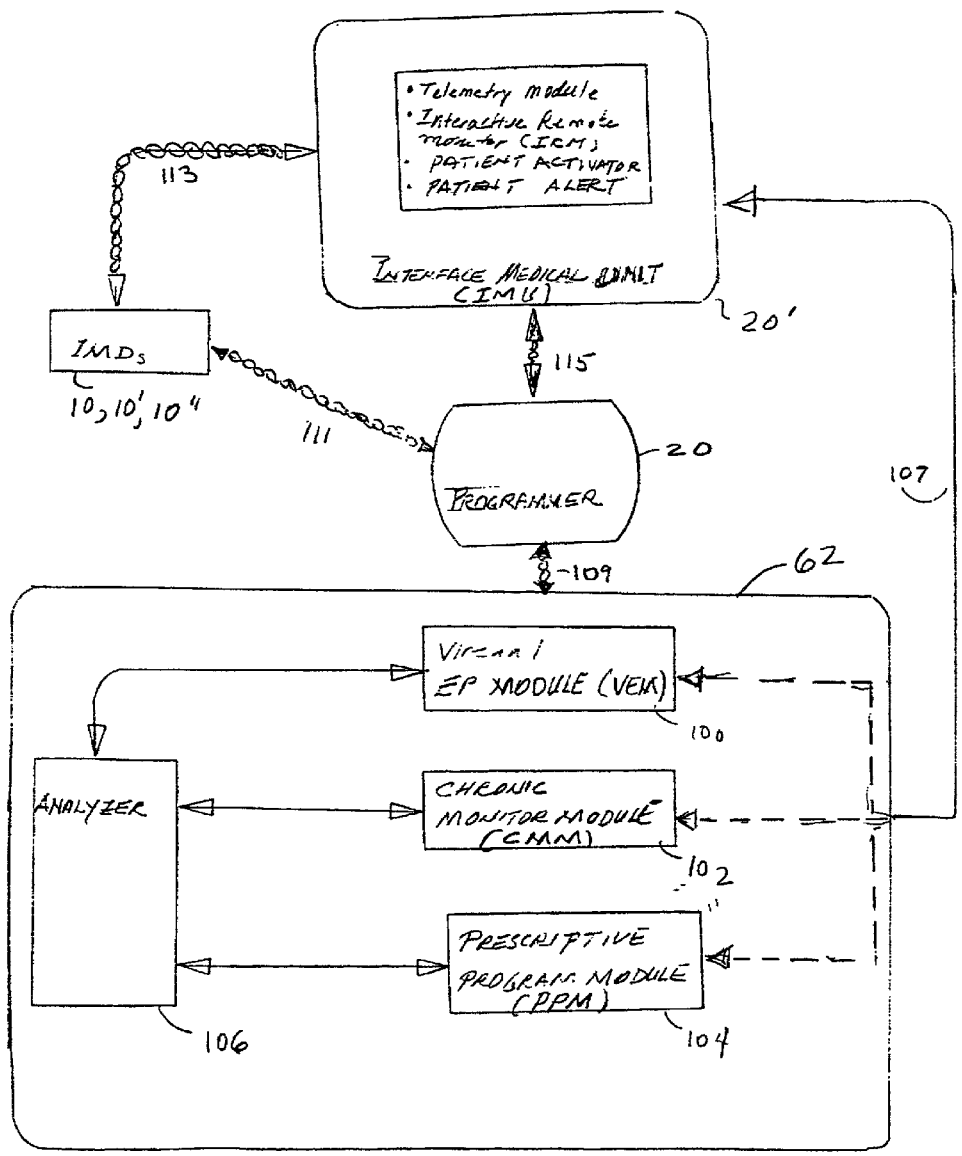
FIG. 4 shows a block diagram illustrating the organizational structure of the wireless communication system, in accordance with one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
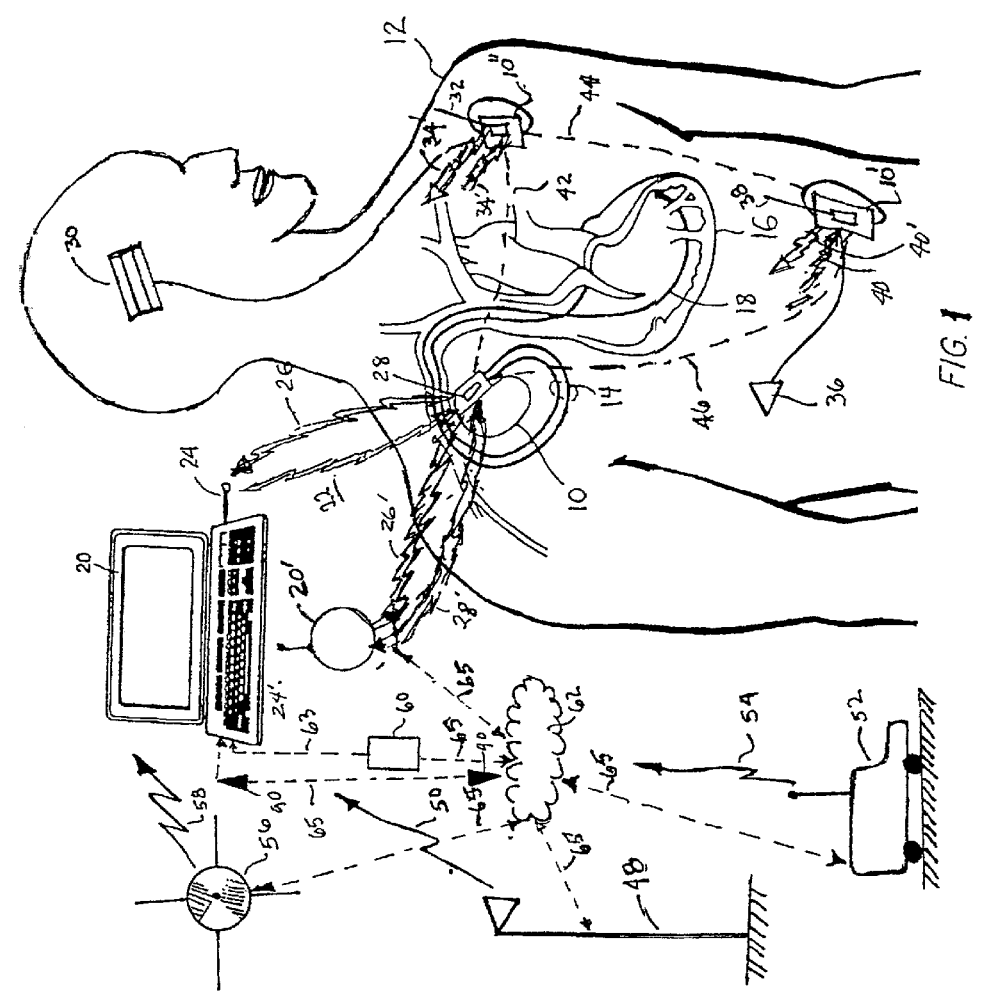

Referring now to FIG. 1, a simplified schematic of the major components a bi-directional wireless communications system is shown. The bi-directional wireless communications system may, in one embodiment, couple a programmer 20, an interface medical unit 20' and a number of implantable medical devices (IMDS) represented by IMD 10, IMD 10' and IMD 10". The IMDs 10, 10', 10" may be implanted in patient 12 beneath the skin or muscle. The IMDs may be electrically coupled to electrodes 18, 30, and 36 respectively in a manner known in the art. IMD 10 may comprise a processor adapted to perform timing, sensing and pacing functions consistent with preset programmed functions. Similarly, IMDs 10' and 10" may comprise processors adapted to provide timing and sensing functions consistent with the clinical functions for which they are employed. For example, IMD 10' may, in one embodiment, provide neural stimulation to the brain via electrode 30 and IMD 10" may function as a drug delivery system that may be controlled by electrode 36.

The various functions of the IMDs 10, 10', and 10" may be coordinated using wireless telemetry. In one embodiment, wireless links 42, 44 and 46 may jointly and severally couple IMDs 10, 10' and 10" such that programmer 20 may transmit commands or data to any or all the IMDs 10, 10' and 10" via one of telemetry antennas 28, 32 and 38. This structure may provide a highly flexible and economical wireless communications system between the IMDs 10, 10' and 10". Further, the structure may provide a redundant communications system, which may enable access to any one of a multiplicity of IMDs 10, 10' and 10" in the event of a malfunction of one or two of antennas 28, 32 and 38.

Programming commands or data may be transmitted from the programmer 20 to the IMDs 10, 10' and 10" via an external RF telemetry antenna 24. The telemetry antenna 24 may be an RF head or equivalent. The antenna 24 may be located on the programmer 20 externally on the case or housing. The telemetry antenna 24 is generally telescoping and may be adjustable on the case of the programmer 20. Both the programmer 20 and the interface medical unit 20' may be placed a few feet away from patient 12 and would still be within range to wirelessly communicate with the telemetry antennas 28, 32 and 38.

The uplink to a remote web-based expert data center 62, hereinafter referred to as, interchangeably, "the data center 62", "the expert data center 62" or "the web-based data center 62" without limitations, is accomplished through the programmer 20 or the interface medical unit 20'. Accordingly the programmer 20 and the interface medical unit 20' function as an interface between the IMDs 10, 10' and 10" and the data center 62. One of the many distinguishing elements of the present invention includes the use of various scalable, reliable and high-speed wireless communication systems to bi-directionally transmit high fidelity digital/analog data between the programmer 20 and the data center 62.

There are a variety of wireless mediums through which data communications could be established between the programmer 20 or the interface medical unit 20' and the data center 62. The communications link between the programmer 20 or the interface medical unit 20' and the data center 62 could be a modem 60, which is connected to the programmer 20 on one side at line 63 and the data center 62 at line 64 on the other side. In this case, data is transferred from the data center 62 to the programmer 20 via the modem 60. Alternate data transmission systems may include, without limitations, stationary microwave and/or RF antennas 48 that may be wirelessly connected to the programmer 20 via tunable frequency wave delineated by line 50. The antenna 48 may be in communications with the data center 62 via a wireless link 65. Similarly, the interface medical unit 20', a mobile vehicle 52 and a satellite 56 may be in communications with the data center 62 via the wireless link 65. Further, the mobile system 52 and the satellite 56 may be in wireless communications with the programmer 20 or the interface medical unit 20' via tunable frequency waves 54 and 58, respectively.

In the preferred embodiment a Telnet system may be used to wirelessly access the data center 62. Telnet emulates a client/server model and requires that the client run dedicated software to access the data center 62. The Telnet scheme envisioned for use with the present invention includes various operating systems including UNIX, Macintosh, and all versions of Windows.

Functionally, an operator at the programmer 20 or an operator at the data center 62 may initiate remote contact. The programmer 20 is down linkable to the IMDs 10, 10', and 10" via the link antennas 28, 32 and 38 to enable data reception and transmission. For example, an operator or a clinician at the data center 62 may downlink to the programmer 20 to perform a routine or a scheduled evaluation of the programmer 20. In this case, the wireless communication is made via the wireless link 65. In the event that a downlink may be required, for example, from the programmer 20 to the IMD 10, the downlink may be created using the telemetry antenna 22. In the event that it may become desirable to initiate an uplink from the patient 12 to the programmer 20, the uplink may be executed via the wireless link 26. As discussed herein below, each antenna from the IMDs 10, 10', 10" may be used to uplink all or one of the IMDs 10, 10', 10" to the programmer 20. For example, the IMD 10" which may relate to a neural implant 30, may be adapted to up-link, via the wireless antenna 34 or the wireless antenna 34', one or more of the IMDs 10, 10', 10" to the programmer 20. Preferably bluetooth chips, which may be adapted to function within the body or outside the body and also adapted to provide low current drain, are embedded in order to provide wireless and seamless connections 42, 44 and 46 between the IMDs 10, 10' and 10". The communication scheme may, in one embodiment, be designed to be broadband compatible and capable of simultaneously supporting multiple information sets and architecture. The communication scheme may further be adapted to transmit at relatively high speed and to provide data, sound and video services on demand.

Referring now to FIG. 2, typical major operative structures that may be found in the IMDs 10, 10' and 10" are represented in a generic format. In the interest of brevity, the IMD 10 relative to FIG. 2 refers to all the other IMDs 10', 10". Accordingly, the IMD 10 is implanted in the patient 12 beneath the patient's skin or muscle and is electrically coupled to the heart 16 of the patient 12 through pace/sense electrodes and lead conductor(s) of at least one cardiac pacing lead 18 in a manner well known to those of ordinary skill in the art. The IMD 10 contains a timing control 72, that may comprise an operating system that may employ a microprocessor 74 or a digital state machine for timing, sensing and pacing functions in accordance with a programmed operating mode. The IMD 10 may also comprise sense amplifiers for detecting cardiac signals, patient activity sensors or other physiologic sensors for sensing the need for cardiac output, and pulse generating output circuits for delivering pacing pulses to at least one heart chamber of the heart 16 under control of the operating system in a manner well known in the prior art. The operating system may, in one embodiment, include one or more memory registers or RAM/ROM 76 for storing a variety of programmed-in operating mode and parameter values that may be used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many may be generally employed to store operating commands and data for controlling device operation and for later retrieval to diagnose device function or patient condition.

Programming commands or data may be transmitted between, for example, the RF telemetry antenna 28 on the IMD 10 and an external RF telemetry antenna 24 associated with the programmer 20. In this case, it is not necessary that the external RF telemetry antenna 24 be contained in a programmer RF head so that it can be located close to the patient's skin overlying IMD 10. Instead, the external RF telemetry antenna 24 may be located on the case of the programmer 20. It should be noted that the programmer 20 may be located some distance away from the patient 12 such that the communication between the IMDs 10, 10' and 10" and the programmer 20 is telemetric. For example, the programmer 20 and the external RF telemetry antenna 24 may be on a stand a few meters or so away from the patient 12. Moreover, the patient 12 may be active and could be exercising on a treadmill or the like during an uplink telemetry interrogation of real-time ECG or other physiologic parameters. The programmer 20 may also be designed to universally program existing IMDs that may employ RF telemetry antennas of the prior art and therefore also have a conventional programmer RF head and associated software for selective use therewith.

In an uplink communication between the IMD 10 and the programmer 20, for example, a telemetry transmission 22 is activated to operate as a transmitter and the external RF telemetry antenna 24 may operate as a telemetry receiver. In this manner data and information may be transmitted from the IMD 10 to the programmer 20. In the alternate, the RF telemetry antenna 26 on the IMD 10 may operate as a telemetry receiver antenna to downlink data and information from the programmer 20. Both the RF telemetry antennas 22 and 26 may be coupled to a transceiver comprising a transmitter and a receiver.

FIG. 3A is a simplified circuit block diagram of major functional components of programmer 20. The external RF telemetry antenna 24 on the programmer 20 may be coupled to a telemetry transceiver 86 and an antenna driver circuit board that may comprise a telemetry transmitter and a telemetry receiver 34. The telemetry transmitter and telemetry receiver 34 are coupled to control circuitry and registers operated under the control of the microcomputer 80. Similarly, within the IMD 10, for example, the RF telemetry antenna 26 may be coupled to a telemetry transceiver comprising a telemetry transmitter and telemetry receiver 34. The telemetry transmitter and telemetry receiver 34 in IMD 10 are coupled to control circuitry and registers that may operate under the control of the microcomputer 74.

Further referring to FIG. 3A, the programmer 20 may be a personal computer type, microprocessor-based device that may include a central processing unit, which may be, for example, an Intel Pentium microprocessor or the like. A system bus may couple the CPU 80 to a hard disk drive that may store operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to the CPU 80 is optionally provided. However the primary communications mode may be through graphics display screen of the well-known "touch sensitive" type controlled by a graphics circuit. A user of the programmer 20 may interact therewith through the use of a stylus, also coupled to a graphics circuit, which may be used to point to various locations on screen or display 84 which display menu choices for selection by the user or an alphanumeric keyboard for entering text or numbers and other symbols. Various touch-screen assemblies are known and commercially available. The display 84 and or the keyboard may comprise means for entering command signals from the operator to initiate transmissions of downlink or uplink telemetry and to initiate and control telemetry sessions once a telemetry link with data center 62 or an implanted device has been established. The display screen 84 may also be used to display patient related data and menu choices and data entry fields used in entering the data in accordance with the present invention as described below. The display screen 84 may also display a variety of screens of telemetered out data or real-time data. The display screen 84 may also display plinked event signals as they are received and thereby serve as a means for enabling the operator to timely review link-history and status.

The programmer 20 may further comprise an interface module, which may include a digital circuit, a non-isolated analog circuit, and an isolated analog circuit. The digital circuit may enable the interface module to communicate with the interface controller module. As indicated hereinabove, the operation of the programmer 20, in accordance with the present invention, may be controlled by the microprocessor 80. The programmer 20 is preferably of the type that is disclosed in U.S. Pat. No. 5,345,362 to Winkler, which is incorporated by reference herein in its entirety.

The display 84 may also display up-linked event signals when received and thereby serve as a means for enabling the operator of the programmer 20 to correlate the receipt of uplink telemetry from an implanted device with the application of a response-provoking action to the patient's body as needed. The programmer 20 may also be provided with a strip chart printer or the like coupled to interface controller module so that a hard copy of a patient's ECG and EGM may be printed.

As will be appreciated by those of ordinary skill in the art, it is often desirable to provide a means for the programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of a Wave unit 90 utilizing laser technologies such as for example the WaveStar Optic Air Unit, manufactured by Lucent Technologies or their equivalent. This embodiment may be implemented for large data transfer at high speed in applications involving several programmers. The unit 90 may comprise a laser 92, a transceiver 94 and an amplifier 96. A first wave unit 90 may be installed at the data center 62 and a second unit 90' may be located proximate to the programmer 20 or the interface medical unit (IMU) 20'. Data transmission between the remote data center 62 and the programmer unit 20 may executed via the first and second wave units 90. Typically, the first wave unit 90 may accept data and split the data into a plurality of unique wavelengths for transmission. The second wave unit 90' may be adapted to recompose the data back to its original form.

FIG. 4 shows a simplified block diagram illustrating the principal systems of the present invention. The Remote expert system or data center 62 may, in one embodiment, comprise a plurality of high speed web-based or web-compatible components. In the context of the present invention, the data center 62 may comprise a virtual electrophysiologist module (VEM) 100, a chronic monitoring module (CMM) 102, and a prescriptive program module (PPM) 104, each being adapted to receive and transmit a two-way communication with an analyzer 106. As discussed hereinabove, the data center 62 may preferably be in wireless communications with the programmer 20. The medium of communications between the programmer 20 and the data center 62 may be selected from one or a combination of several cable and wireless systems discussed hereinabove. Further, the programmer 20 may be in wireless communications with a number of IMDs 10, 10', 10", such as shown in FIG. 1. Although three IMDs 10, 10', 10" are shown for illustrative purposes, it should be noted that several IMDs may be implemented and the practice of the present invention in no way limits the number of implants. The data center 62 may also be in wireless communications with programmer 20 via link 109. Further, programmer 20 may be in wireless data communications with the IMDs 10, 10' and 10" and the IMU 20' via links 111 and 115 respectively. As will be discussed herein below, in an alternate embodiment relating to special applications, the IMU 20' could be in direct wireless or data communications with the data center 62 and the IMDs 10, 10' and 10" via links 107 and 113, respectively.

Figure 5:
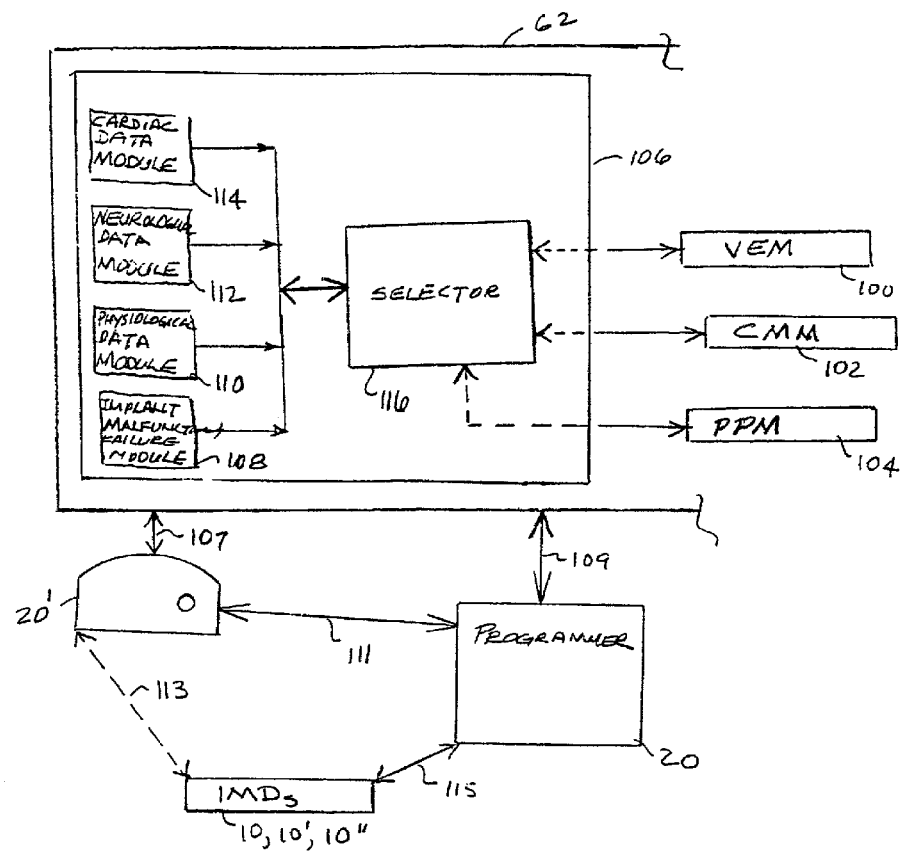
FIG. 5 is a block diagram illustrating a detail section of an analyzer that may be used in the wireless communication system shown in FIG. 4, in accordance with one embodiment of the present invention.

FIG. 5 shows stylized block diagram of a more detailed representation of the relevant elements of analyzer 106. Specifically, in the context of the present invention, analyzer 106 may comprise an implant device malfunction or failure alert module 108, a physiological data module 110, a neurological data module 112 and a cardiac data module 114. However, it should be noted that the number and/or location of the modules 108, 110, 112, 114 is not material to the present invention and more or fewer modules may be used by the analyzer 106 without changing the spirit or scope of the present invention. The modules 108, 110, 112, 114 may be in a bi-directional data and electronic connection with a selector 116. Further, the selector 116 may be in operable two-way data communication with the VEM 100, the CMM 102 and the PPM 104. As indicated hereinabove, the programmer 20 may be in bi-directional wireless communications with the data center 62 via link 109. The programmer 20 may also be in two-way wireless communication with the IMDs 10, 10', 10" and the IMU 20' via link 115 and link 111, respectively.

Referring to the programmer 20 in more detail, when a physician or an operator needs to interact with the programmer 20, a keyboard that may be coupled to the CPU 80 may optionally be employed. However, the primary communication mode may be through graphics display screen of the well-known "touch sensitive" type controlled by graphics circuit. A user of the programmer 20 may interact therewith through the use of a stylus also coupled to a graphics circuit, which may be used to point to various locations on the screen/display to display menu choices for selection by the user or an alphanumeric keyboard for entering text or numbers and other symbols as shown in the above-incorporated '362 patent. Various touch-screen assemblies are known and commercially available. The display and or the keyboard of the programmer 20 preferably include means for entering command signals from the operator to initiate transmissions of downlink telemetry from the IMDs 10, 10', 10" and to initiate and control telemetry sessions once a telemetry link with one or more of the IMDs 10, 10', 10" has been established. A graphics display/screen is also used to display patient related data and menu choices and data entry fields used in entering the data in accordance with the present invention as described below. The graphics display/screen may also display a variety of screens of telemetered out data or real-time data. The programmer 20 may also be provided with a strip chart printer or the like, which may be coupled to interface controller module so that a hard copy of a patient's ECG, EGM, marker channel or similar graphics display can be generated. Further, the functional and data communications event and history of the programmer 20 relating to instrumentation and software status may be printed from a printer. Similarly, once an uplink is established between the programmer 20 and any one of the IMDs 10, 10' and 10", various patient history data and IMD performance data may be printed out. Although not so limited, the IMDs 10, 10', 10" contemplated by the present invention may include a cardiac pacemaker, a defibrillator, a pacer-defibrillator, implantable monitor, cardiac assist device, and similar implantable devices for cardiac rhythm and therapy. Further the IMD units contemplated by the present invention may include electrical stimulators such as, but not limited to, a drug delivery system, a neural stimulator, a neural implant, a nerve or muscle stimulator or any other implant designed to provide physiologic assistance or clinical therapy.

As indicated hereinabove, the data center 62 may represent a high speed computer network system which may be located remotely and may communicate via wireless bi-directional data, voice and video communications with the programmer 20 and the IMU 20'. Generally, the data center 62 may be located in a central location and may be equipped with high-speed web-based, web-enabled or web-compatible computer networks. Preferably, the data center 62 may be manned 24-hours by operators and clinical personnel who are trained to provide a web-based remote service to the programmer 20 and the IMU 20' to thereby ensure chronic monitoring, prescriptive programming and implementation of virtual electrophysiological functions remotely. Additionally, as discussed hereinabove, the data center 62 may include other resources and features to provide remote monitoring, maintenance, and upgrade of the programmer 20. The location of the remote data center 62 may depend upon the sphere of service. In accordance with the present invention, the data center 62 may be located in a corporate headquarters or manufacturing plant of the company that manufactures the programmer 20. Further, the wireless data and electronic communications link/connection can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, the bi-directional wireless communications 109 may act as a direct conduit for information exchange between the remote data center 62 and the programmer 20. Further, the bi-directional wireless communications 109 may provide an indirect link between the remote data center 62 and the IMDs 10, 10' and 10" via the programmer 20. In the context of this disclosure the word "data" when used in conjunction with the bi-directional wireless communications 109 also refers to sound, video and information transfer between the various functional units.

Figure 6:
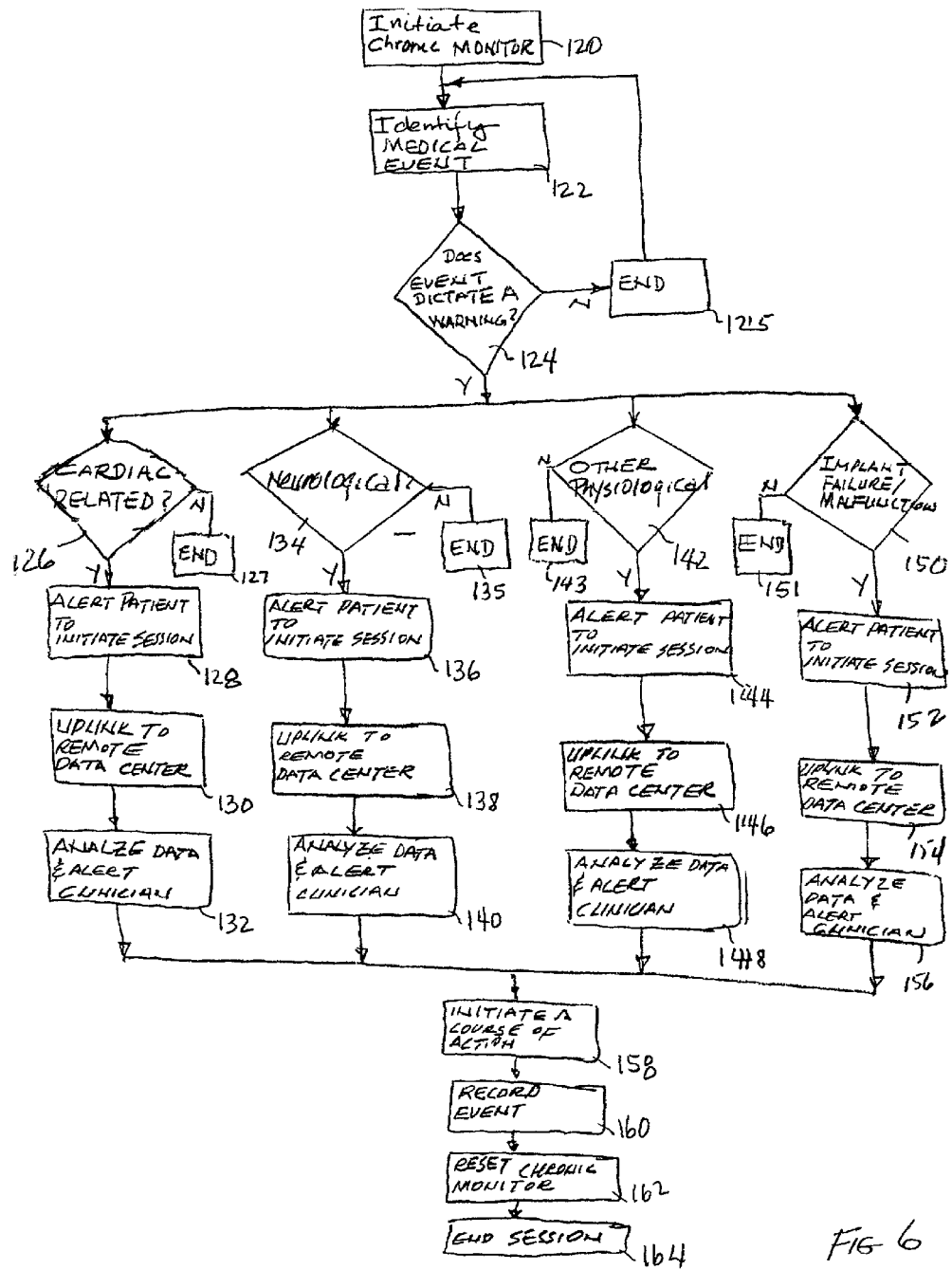
FIG. 6 represents a high level software logic for implementing chronic monitoring functions in the wireless communication system shown in FIG. 4, in accordance with one embodiment of the present invention.

Referring now to FIG. 6, a logic flow chart illustrating a method for running the CMM 102 that may be encoded in a software package is displayed. Specifically, the method is implemented by initiating the CMM 102 under logic step 120. The logic identifies a medical event under logic step 122. This is primarily done by communicating to the IMDs 10, 10' and 10" via the programmer 20 and or the IMU 20' to determine a prevailing medical condition. In a consequent logic step, the program goes into decision step 124 where the need for a warning, based on the medical event noted, is evaluated. If the evaluation indicates that the event does not require the issuance of a warning, the logic step may end the query under logic step 125 and may go into a waiting subroutine for the next signal. In the alternate, if a warning is warranted, the program may proceed to evaluate the need for whether the event relates to cardiac, neurological, other physiological and/or failure of any of the IMDs 10, 10', 10". Under the warning process, the program may advance to decision step 126 to check if the alert relates to cardiac data module 114. If not, the query may be terminated at step 127. If the relates to cardiac data module 114, however, the program logic may proceed to logic step 128 where the patient is alerted to initiate a session. The alert may be sent via the two way communication links from the web-enabled data center 62 to either the programmer 20 or the IMU 20'. Accordingly, one or all of the IMDs 10, 10' and 10" may be up-linked to the remote data center 62 under logic step 130. Particularly, the data may be directed to cardiac data module via selector 11 in analyzer 106. Thereafter, the data may be analyzed and the clinician notified under logic step 132. Similarly, if the warning or medical event relates to neurological clinical care or therapy, the logic may proceeds to decision step 134. The query may be terminated if the medical event is not neurological. If neurological, however, the logic may proceed to logic step 136 to prompt the patient to initiate a session. Under this scenario, the patient may uplink to the data center 62 via the programmer 20 or the IMU 20" which process is described under logic step 138. Specifically, the data may be routed via the selector 116 to the neurological data module 112 where the data may be analyzed and the physician or clinician may be alerted in accordance with logic step 140. Similarly, if the medical event relates to other physiological diagnosis and clinical care, the logic may proceed to decision step 142. Consistent with the program logic described hereinabove, the logic may proceed to end the query under step 143 if the medical event does not relate to physiological aspects of the clinical care regimen. If it concerns physiological aspects, however, the program logic may proceed to logic step 144 to alert the patient to initiate a session. The patient's device may then be up-linked to the remote data center 62 under logic step 146. Subsequently, the data may be analyzed and a clinician alerted under logic step 148. Similarly, if the medical event relates to a noted malfunction or failure of any one or all of IMDs 10, 10' and 10", the program logic may proceed to decision block 150. The patient may be alerted under logic step 152. Subsequently, the data may be transferred from the IMD 10, 10', 10" in question to the data center 62, under logic step 154, in the manner described hereinabove. The data may then be analyzed and a clinician notified under logic step 156.

Thereafter, depending on the medical event at hand which may include one, all or any combinations thereof, the system may initiate a course of action under logic step 158. The event may be recorded under step 160. Thereafter, the chronic monitor may be reset under logic step 162 and the session may end at logic step 164.

The implementation of a chronic monitoring scheme is one of the significant features of the wireless communications and data exchange system advanced by the present invention. Specifically, chronic monitoring is implemented via the CMM 102 that may contain the software to manage the data stream from any of the IMDs 10, 10', 10" on a real time basis. Further, the system may enable the development of a data bank as it relates to both the therapy and diagnostic aspects of the IMDs 10, 10', 10". The selector 116 may route data input from the CMM 102 and further enable routing the data to the relevant module, i.e., device diagnosis module 108, physiological data module 110, neurological data module 112 and cardiac data module 114. The CMM 102 may be in data communications with the programmer 20 and the IMU 20'. Further, the IMDs 10, 10' and 10" may preferably be in data communications with the programmer 20 and the IMU 20'. In the preferred embodiment, the IMU 20' may be a handheld web-top device with telemetric communication capabilities to exchange data to and from the IMDs 10, 10' and 10". Thus, the IMU 20' could be a low-level version of the programmer 20 having, for example, the ability to interact with the IMDs 10, 10' and 10". Accordingly, the CMM 102 may monitor the IMDs 10, 10' and 10" remotely through the programmer 20 and/or the IMU 20' via wireless links 109 and 107 respectively.

In an alternate embodiment, the IMU 20' may operate as an intermediate data exchange unit located with the patient. In this context, the programmer 20 may be located remotely and would be in communication with the IMU 20' and would be used to interact with the data center 62.

Figure 7A:
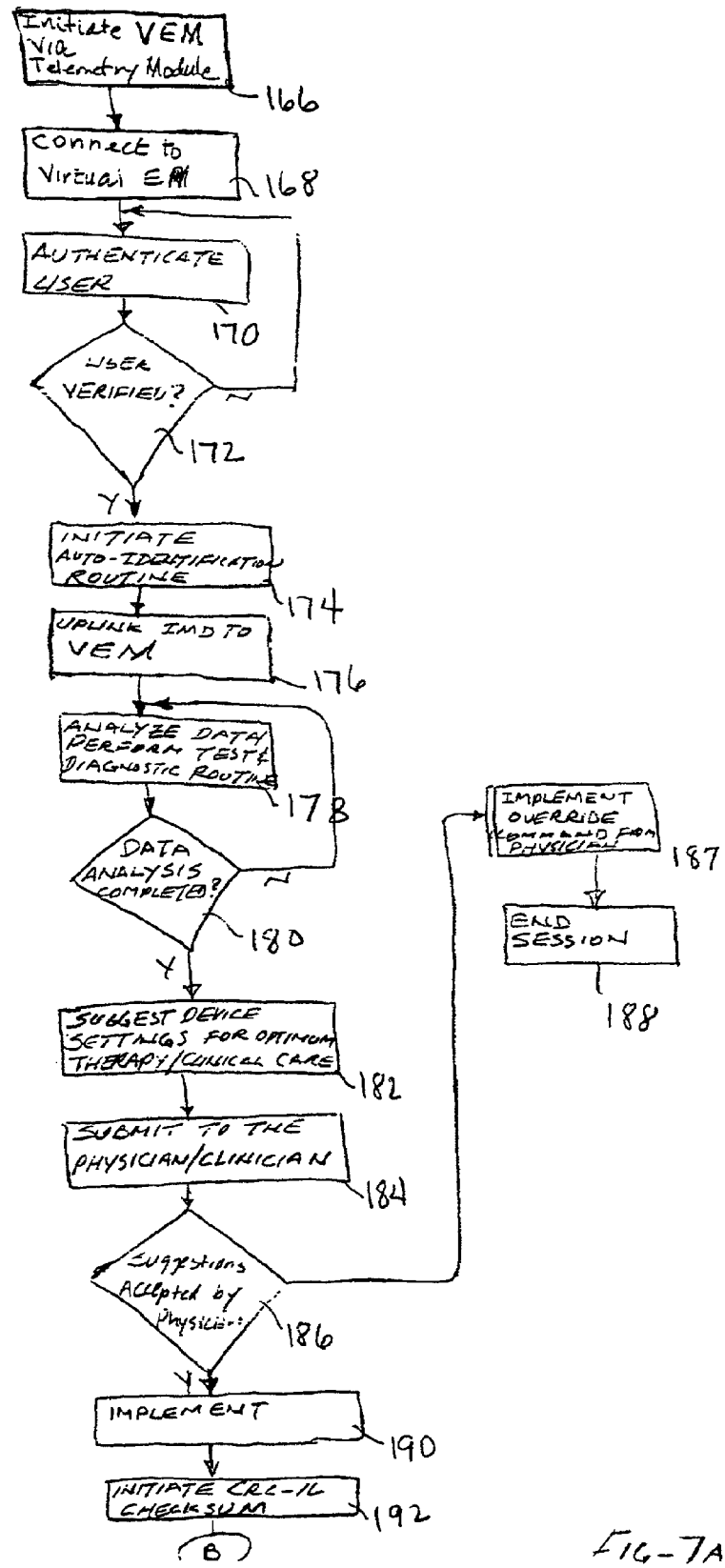
FIGS. 7A and 7B represent a high level software logic for implementing a virtual electrophysiologist module in the wireless communication system shown in FIG. 4, in accordance with one embodiment of the present invention.
Figure 7E:
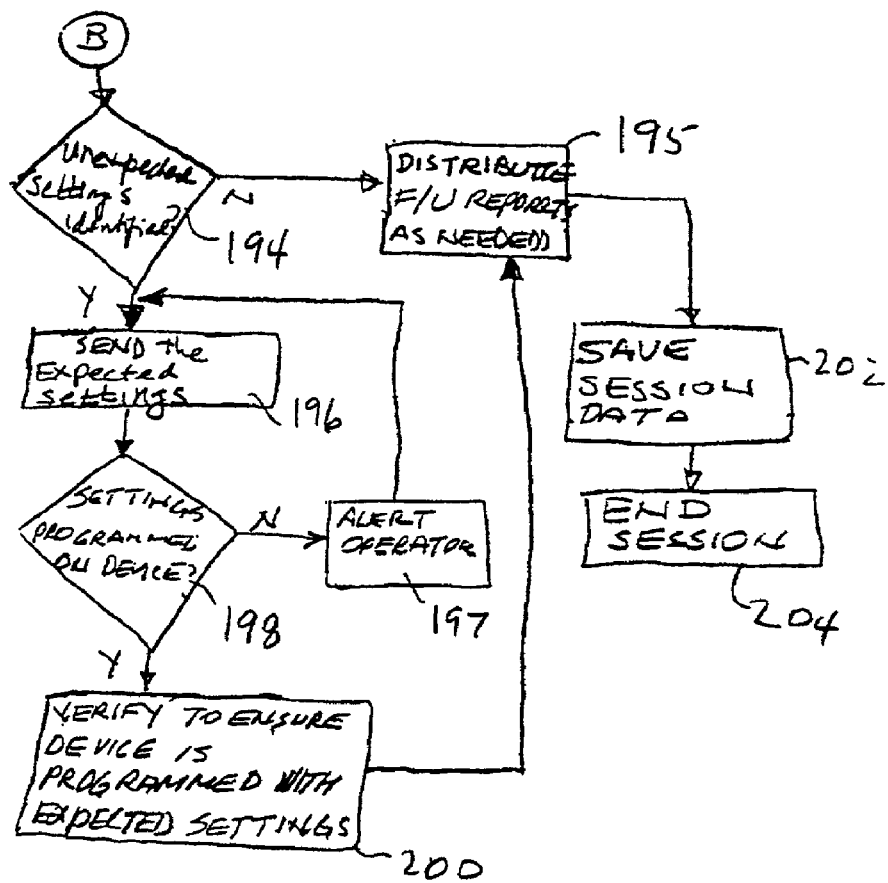
Figure 26:
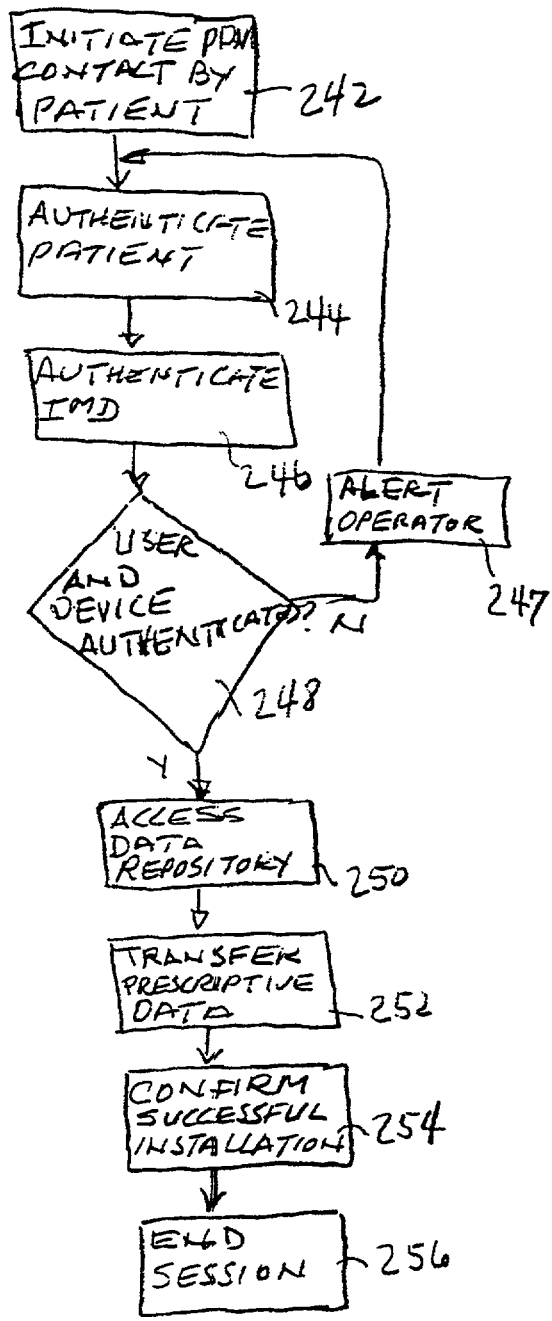

Referring to FIGS. 7A and 7B, a software logic chart is represented showing one implementation of the VEM 100 that may effect a continuous monitoring of the IMDs 10, 10' and 10" for remotely adjusting the settings of the implanted devices to promote optimum therapy and clinical care. The logic starts at step 166 where the VEM 100 may be initiated via telemetry or equivalent wireless communication system. Subsequently, under logic step 168, either the programmer 20 or the IMU 20' may be connected to the VEM 100. Further, the user may be authenticated, under logic step 170, before further access to information and operations in the remote data center 62 may be permitted. The logic may proceeds to decision block 172 to check if the user has been verified. It should be noted that the VEM 100 may be used as a continuous, follow-up or real time system to enable adjustment of critical parameters of the IMDs 10, 10' and 10" in real-time. Returning to decision block 172, if the user is not verified, the logic may revert back to step 170 where authentication of the user is requested. If after a few trials the user is not verified, the program may terminate and display a message asking the user to call the operator or some other authority. In the event the user is authenticated, the logic may proceed to step 174 where the auto identification routine is activated. The logic may then uplink the IMDs 10, 10' and 10" to the VEM 100 via telemetry or equivalent wireless communications system. It should be noted that the VEM 100 may be connected to the IMDs 10, 10' and 10" indirectly via the programmer 20 and/or the IMU 20". When the IMDs 10, 10' and 10" are up-linked to VEM 100, the VEM may gain access to the data base and information exchange. Primarily, VEM 100 may operate on data relating to the functional aspects of components in the IMDs 10, 10', 10". More specifically, the VEM 100 may monitor and be able to virtually and in real-time review the status of designated components of the IMDs 10, 10', 10". Accordingly under logic step 178, the program logic may analyze data, perform tests, and execute diagnostic routines. Subsequently, the program logic may check to see whether the data analysis has been substantially completed under decision block 180. If the analysis is incomplete, the logic may revert back to step 178. If the analysis is completed, a recommendation may be made for device settings to deliver optimal therapy or clinical care under logic step 182. The recommendation may then be submitted to the physician or clinician under logic step 184. The physician may render an opinion, under decision block 180, as to whether the recommendation is acceptable based on current medical practice or accepted standards relating to the setting and the therapy or care for which the settings are to be made. If the recommendation is not accepted or approved by the physician, the software logic may advance to logic step 187 where an override is set to implement the recommendation of the physician as to the desirable settings and the session may be terminated at logic step 188. In the alternate, if the physician approves the recommendation it may be implemented under logic step 190. Subsequently, the logic proceeds to step 192 where a CRC-checksum may be used to make sure that the data has not changed or is false. Preferably, a 16-bit CRC may be created by initializing a check-variable to set the CRC-checksum. The logic may proceed to decision block 194 where the software checks for any unexpected settings which may be identified. At this point in the logic, the system may utilize a redundant data check, via the CRC and decision block 194 to ensure that the remote setting data is accurate and uncorrupted. If an unexpected setting is identified, the logic may proceed to step 195 where a follow-up report (F/U) may be distributed to the physician and other personnel for review and investigation of the unexpected settings and the source of the data corruption. Thereafter, the system may save the session data under logic step 202 and terminate the session at step 204. In the alternate, if there are no unexpected settings are identified, the expected settings may be sent, under logic step 196, to the device via telemetry or equivalent wireless communications system. Subsequently, the logic may advance to decision step 198 where the system may check if the remotely transferred settings data have been substantially implemented on one or more of IMDs 10, 10' and 10", via the programmer 20 or the IMU 20', as needed. If not, the operator may be alerted under logic step 197, and also may attempt to send the data by reverting back to logic step 196. After a predetermined number of attempts to send the data, the system may interrupt the sequence and post a note to the operator. Under logic step 200, the system may verify that the programmer 20, the IMU 20', and the IMDs 10, 10' and 10" have been programmed with the respective expected settings. Thereafter, the logic may proceed to distribute follow up reports as needed under logic step 195. The session data and file history may be saved under step 202. Subsequently, the session may be terminated under logic step 204.

The VEM 100 may be implemented to remotely monitor the settings of a plurality of medical devices in a patient. Particularly, the VEM 100 may be located remotely in a preferably web-enabled high capacity and high speed computer environment such as the data center 62. The VEM 100 may operate as one of the therapeutic/clinical arms of the present invention. The VEM 100 may specialize in monitoring the critical and optimal settings in medical devices on a continuous basis. This is particularly important in patients with multiple implants because the range of settings of one device may not be compatible with the settings of other devices. Thus, the VEM 100 may be implemented to set, coordinate and monitor the various settings in a multiple-implant medical device environment.

Referring now to FIGS. 8A and 8B, a flow chart illustrating a method that may be used to operate the PPM 104 is shown. As discussed hereinabove, the PPM 104 relates to a remote programming of IMDs 10, 10' and 10" to install prescriptive functions. Specifically, the scheme relates, inter alia, to the remote installation of data that is in a repository as part of a recommended medical upgrade or alterations to IMDs 10, 10' and 10".

The PPM software may be initiated by the physician under logic step 210. Subsequently under logic step 212 a secure mode may be activated which may, in one embodiment, include an encrypted operative to ensure security. The user may then be authenticated under logic step 214. The secure mode may trigger the decision step 216 where the authenticity of the user is verified. If the user is not verified, the session may be terminated under logic step 215. If the user is authenticated, access to an existing data repository may be allowed under logic step 218. The menu includes an option to add new prescription data under decision block 220. If the session does not concern the addition of new prescription data, the logic may proceed to step 221 and the session may be terminated. However, in the event that it may be desirable to add a new prescription, the logic may install the required data under logic step 222. Thereafter, the accuracy of the data may be confirmed under logic 224. The session for installing a new set of prescription data ends at logic step 226.

In the alternate, if the session concerns the review of patient data to ultimately install prescriptive data and/ or review the data to develop a new set of prescriptive data based on the performance history of the IMDs 10, 10' and 10", the menu may provide the option to move to decision step 228. If that option is not selected, the session terminates at step 229. In the event the user elects to review the patient data and ultimately install a prescriptive program as needed, the logic may proceed to step 230 where the data may be upgraded, altered or enhanced based on the patient history and other clinical parameters and decisions. The alterations and modifications may be installed in the patient file under logic step 232. Thereafter, the physician may call the patient under logic step 232 to inform to the patient that a new program will be installed remotely. Consequently the new program may be transferred via wireless communication systems, in the manner described hereinabove, under logic step 236. The transfer may then be recorded under logic step 238 and the session terminates at logic step 240.

In an alternate embodiment, after the physician notifies the patient of the need to install a new program, the patient may initiate contact with PPM 104 to transfer the recommended data. Accordingly, referring to FIG. 8B, the patient initiates contact under logic step 242. The system authenticates the patient under logic step 244. Further the system authenticates the one or more IMDs 10, 10', 10" which may be implanted in the patient. The logic proceeds to decision step 248 to determine if both the patient and the one or more IMDs 10, 10', 10" are authenticated to access the specific patient data and the relevant prescriptive program file. If such is not the case, the system may alert the operator under logic step 247 and deny access to the user. If, however, both the user and the one or more IMDs 10, 10', 10" are substantially authenticated, access to data repository may be allowed under logic step 250. Prescriptive data may then be remotely transferred under logic step 252. Further, successful installation may be confirmed under step 254. Logic step 254 contains subsets wherein if a successful installation is not confirmed after a predetermined number of attempts, a flag may be set to alert the operator and terminate the session after informing the patient about system malfunctions. Once a successful installation is confirmed, however, the logic proceeds to step 256 where the session terminates.

Thus, PPM 104 provides a set of data that is prescriptive in nature. Specifically, the PPM data set relates to clinically recommended upgrades and modifications which are integrated with patient history, performance of the IMDs 10, 10', 10" in the patient and similar clinical data. Generally, in the context of the present invention, prescriptive data is updated and upgraded by the physician thus forming a medical data repository specific to the patient and the devices implanted in the patient. When the need to install a new prescriptive program arises, the remote installation session may be initiated by the physician or the patient. When initiated by the physician, the patient needs to be informed such that either the programmer 20 or the IMU 20' may be set to accept the prescriptive data via wireless communication system, in the manner described hereinabove. The prescriptive program will then be transferred from the programmer 20 and/or the IMU 20' via telemetry communications with the IMDs 10, 10' and 10".

Figure 9A:
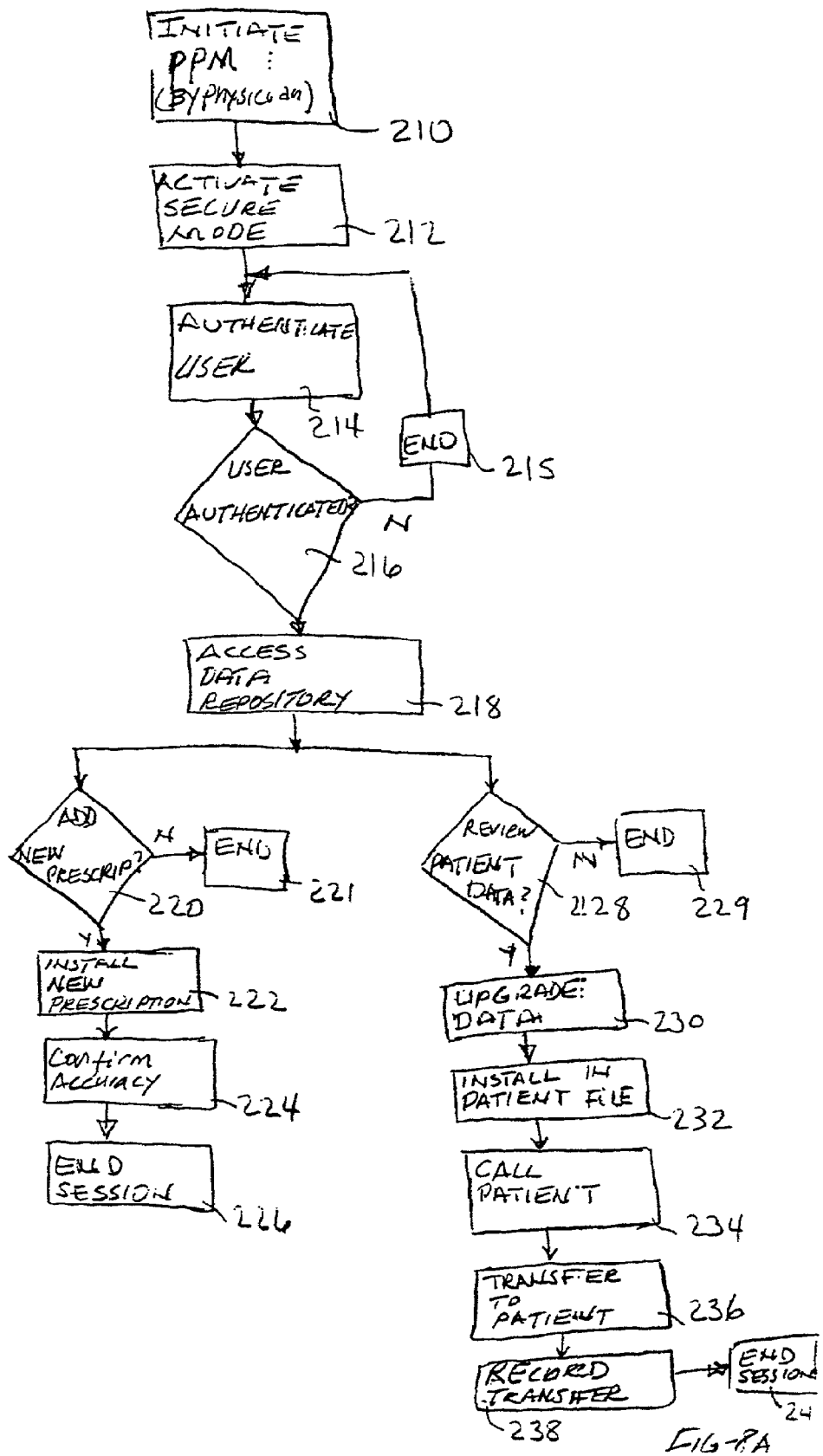
FIG. 9 shows a stylized block diagram of remote programming system that may be used in conjunction with the bi-directional wireless communication system depicted in FIG. 1 is shown, in accordance with one embodiment of the present invention.
Figure 9:
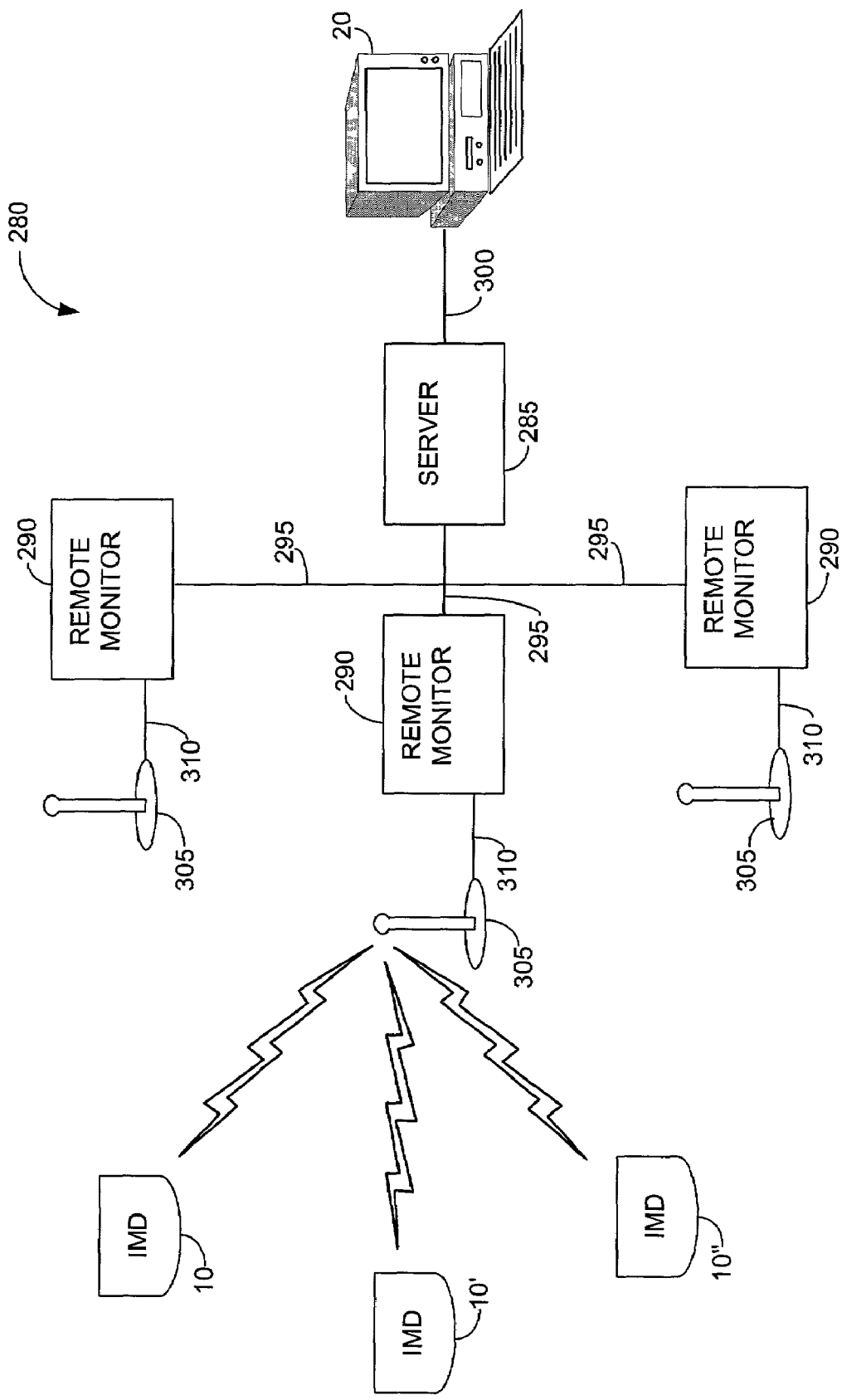

Referring now to FIG. 9, a stylized block diagram of remote programming system 280 that may be used in conjunction with the bi-directional wireless communication system depicted in FIG. 1 is shown. The remote programming system 280 may, in one embodiment, comprise a processor-based server 285 coupled to one or more remote monitors 290 by one or more lines 295. The server 285 may comprise one or more processors and one or more memory elements, and may be adapted to communicate with the programmer 20 through a line 300. Each remote monitor 290 may similarly comprise one or more processors and one or more memory elements, and may be adapted to communicate with a plurality of IMDs 10, 10', 10" through an antenna 305 that may be coupled to the remote monitor 290 by a line 310. Although not so limited, the lines 295, 300, 310 may comprise a physical connection capable of transmitting electric signals (e.g. wires or cables) or a wireless telemetry, as described above.

The remote monitors 290 may be placed at substantially any location that allows the remote monitor 290 to maintain a reasonably continuous connection to the server 285 through the line 295. Exemplary locations may include, but are not limited to, the patient's home and a clinic. Hereinafter, a remote monitor 290 that may be ordinarily located in the patient's home will be referred to as an "in-home" remote monitor 290 and a remote monitor 290 that may be ordinarily placed in a clinic will be referred to as an "in-office" remote monitor 290.

A clinician may be responsible for the treatment of a plurality of patients. Various organs and/or tissues in the patients may be monitored or treated by one or more IMDs 10, 10', 10". As described above, in one embodiment, the IMDs 10, 10', 10" may comprise a processor that may run a software package. From time to time, it may become desirable to program or reprogram the processor to improve the treatment that may be provided by the IMDs 10, 10', 10". As it may not always be convenient, necessary, or even possible for the patients and clinicians to be present at substantially the same place and at substantially the same time, it may be desirable to adapt the remote programming system 280 to receive and store programming instructions from the clinician which may be transmitted to the IMDs 10, 10', 10" at a later time.

Figure 10A:
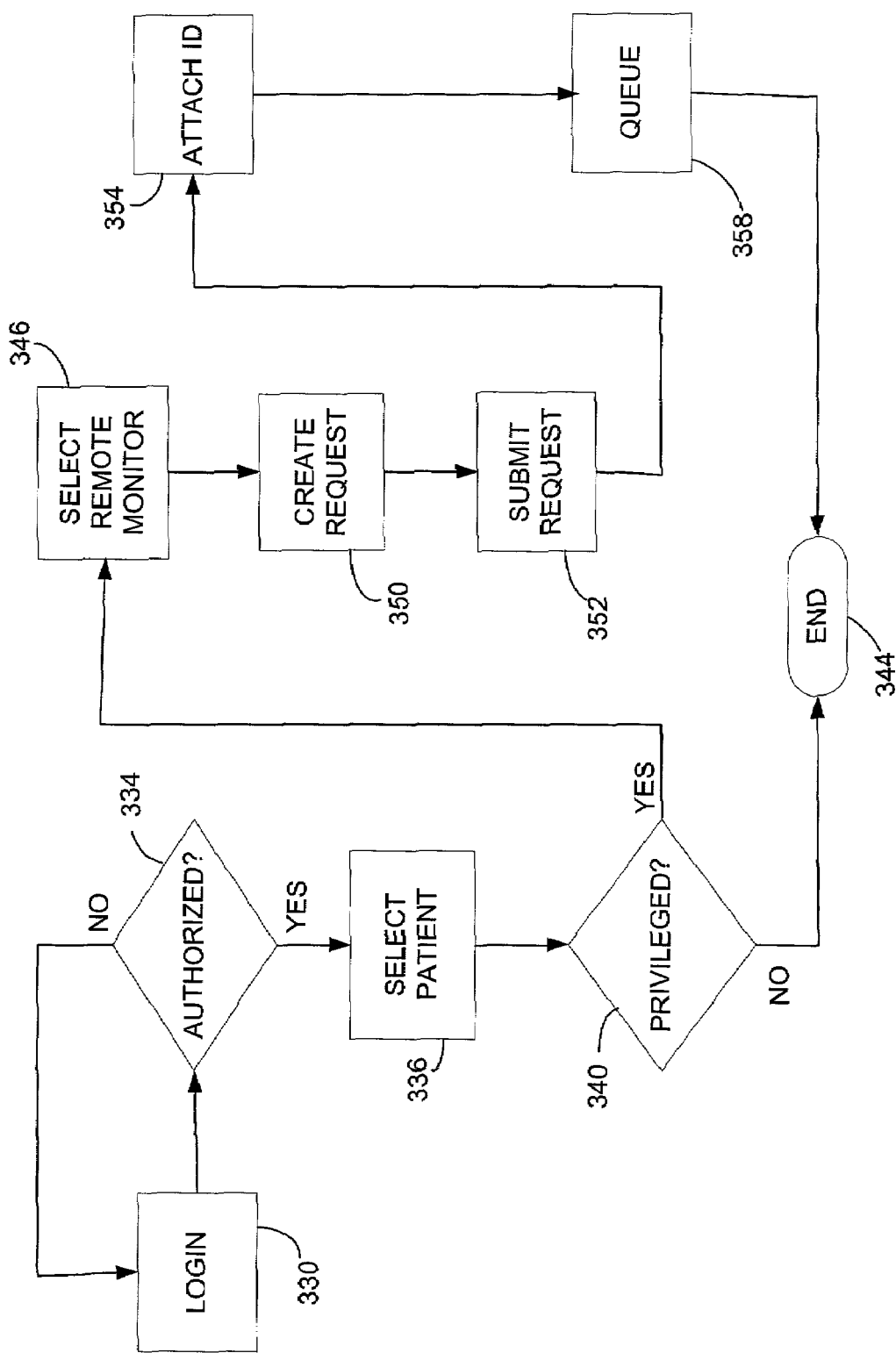
FIGS. 10A–C show three flow diagrams illustrating a method that may be used for remotely programming an IMD using the remote programming system described in FIG. 9, in accordance with one embodiment of the present invention.
Figure 10B:
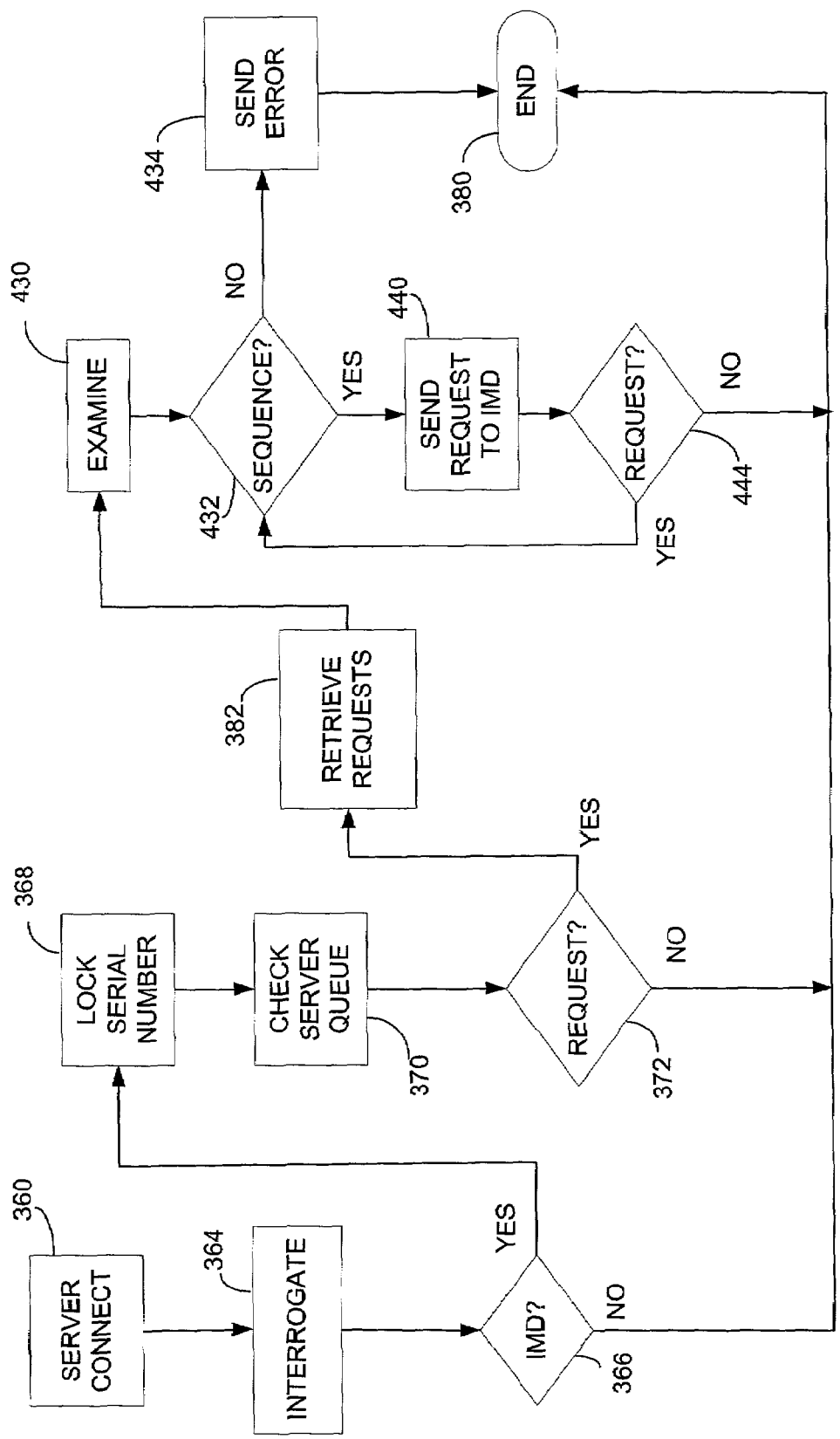
Figure 10C:
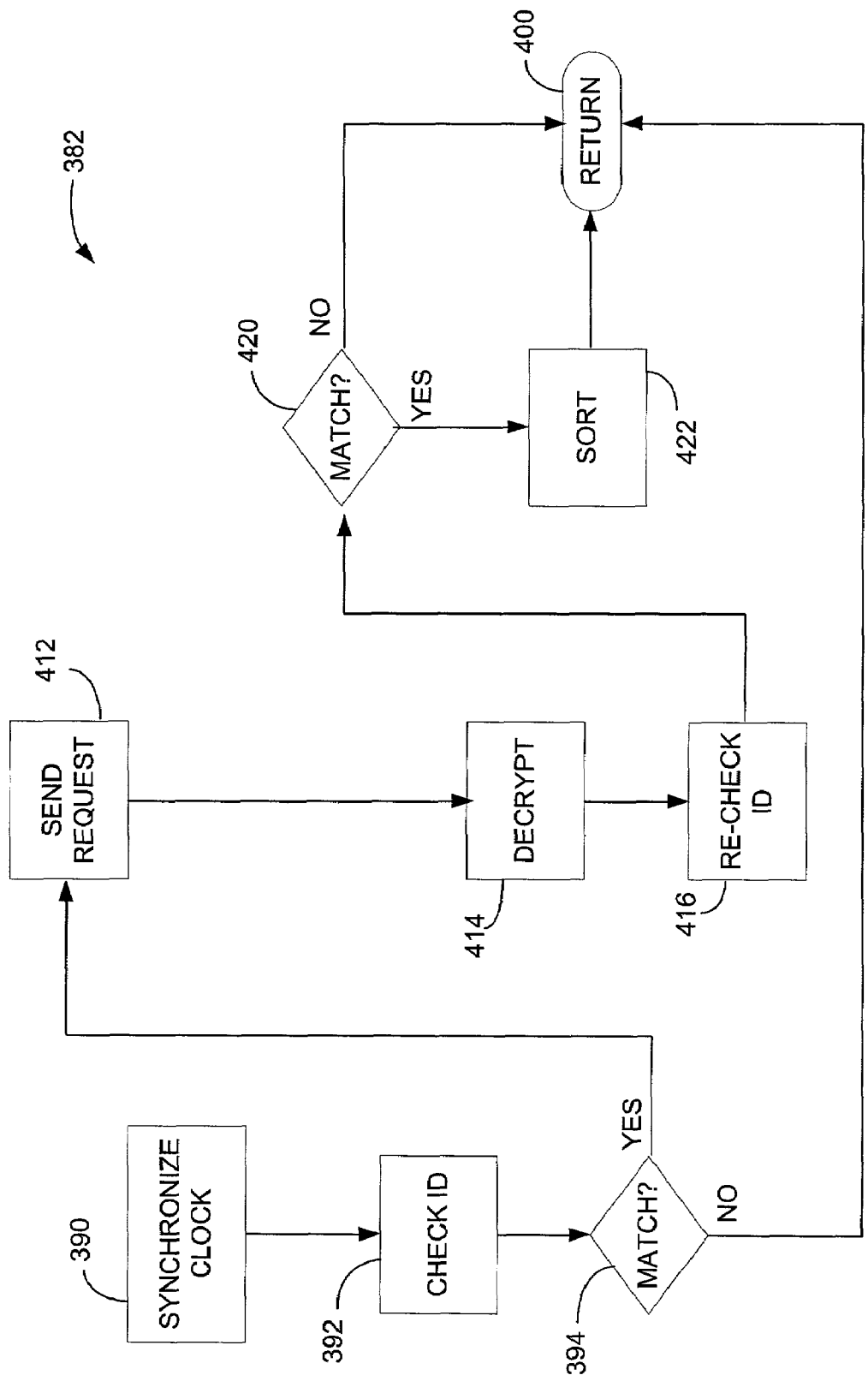

FIGS. 10A–C show flow diagrams illustrating a method that may be used for remotely programming an IMD 10, 10', 10" using the remote programming system 280 depicted in FIG. 9. Referring now to FIG. 10A, a flow chart illustrating a method of creating new programs for an IMD 10, 10', 10" that may be stored for a selected duration is shown. In one embodiment, a clinician operating the programmer 20 may log in (at 330) to the server 285 of the remote programming system 280. Using any one of a variety of standard user-authentication or password-protection schemes well known to those of ordinary skill in the art, the server 285 may authorize (at 334) the clinician to use the server 285. For example, in one embodiment, the server 285 may authorize (at 334) the clinician by requesting a user ID and password from the clinician. If the server 285 is substantially unable to authorize (at 334) the clinician, the server 285 may, in one embodiment, prompt (at 330) the clinician to try again.

Once the clinician has been authorized (at 334) to use the server 285, the clinician may, in one embodiment, select (at 336) a patient. The patient may have one or more implanted IMDs 10, 10', 10" that it may be desirable to program. Using any one of a variety of standard user-authentication or password-protection schemes well known to those of ordinary skill in the art, the server 285 may verify (at 340) that the clinician has the correct privileges that may allow the clinician to program the IMDs 10, 10', 10". If the server 285 determines (at 340) that the clinician may not possess the privileges that may allow the clinician to program the IMDs 10, 10', 10", the server 285 may end (at 344) the session.

However, in one embodiment, if the server 285 determines (at 340) that the clinician may possess the privileges that may allow the clinician to program the IMDs 10, 10', 10", the clinician may then select (at 346) a remote monitor 290. Although not so limited, the selected remote monitor 290 may be an in-home remote monitor 290 or an in-office remote monitor 290. The clinician may then use the programmer 20 to create (at 350) a request that may, in one embodiment, comprise data and or at least one instruction that may be used by the IMDs 10, 10', 10" to change some aspect of the operation of the IMDs 10, 10', 10". For example, in one embodiment, the request may comprise instructions that enable the IMDs 10, 10', 10" to change the voltage that may be delivered to an arrhythmic heart.

The programmer 20 may then submit (at 352) the request to the server 285. The server 285 may then, in one embodiment, attach (at 354) one or more identifying tags to the request. Although not so limited, the identifying tags may contain such information as the serial number of the IMD 10, 10', 10" and the remote monitor 290. The server may then place (at 358) the request in a queue, where it may be available to the remote monitor 290 at substantially any time.

The request may be transmitted to the IMD 10, 10', 10" via the remote monitor 290 in response to a signal from the clinician, a process referred to hereinafter as "in-clinic" programming. In one embodiment, the clinician may cancel any requests that may be pending or substantially incomplete before submitting the signal that may cause the request to be transmitted to the IMD 10, 10', 10". The request may alternatively be stored in the queue until such a time as the patient may determine that it may be desirable to remotely program the IMD 10, 10', 10", a process referred to hereinafter as "in-home" programming.

Turning now to FIG. 10B, a flow chart illustrating a method for retrieving programming requests from the server 285 is shown. In one embodiment, the illustrated method may be used for both in-clinic and in-house programming. At such a time as it may become desirable to remotely program an IMD 10, 10', 10", the remote monitor 290 may establish (at 360) a connection to the server 285 via the line 295. As discussed above, the line 295 may comprise any one of a variety of means of coupling the remote monitor 290 to the server 285 well known to those of ordinary skill in the art. For example, in one embodiment, the line 295 may comprise at least one of a telephone line, an intranet, an internet, a satellite, and a global positioning system.

Public and private networks 110, 120 may be vulnerable to imposters, variously referred to hereinafter as "rogues" or "hackers", who may penetrate the networks 110, 120. In the event that the rogues or hackers penetrate the networks 110, 120, they may send erroneous messages to the server 285 and/or the remote monitor 290. The erroneous messages may, in one embodiment, be transmitted to the IMDs 10, 10', 10", and may thus potentially endanger the patient. Thus, it may be desirable to provide a secure connection between the server 285 and the remote monitor 290. The secure connection may, in one embodiment, be established using any one of a variety of cryptographic, password-protection, or user-authentication schemes well known to those of ordinary skill in the art. For example, in one embodiment, the remote monitor 290 may communicate (at 360) with the server 285 using a Virtual Private Network (VPN). In one alternative embodiment, the remote monitor 290 may communicate (at 360) with the server 285 using a Secure Socket Layer (SSL) connection. Using the secure connection may reduce the chance the rogues or hackers may transmit erroneous, and potentially life-threatening to the patient, messages to the server 285 and/or the remote monitor 290.

The remote monitor 290 may also, in one embodiment, interrogate (at 364) nearby IMDs 10, 10', 10". Although not so limited, interrogation may comprise scanning a range of radio frequencies to detect signals that may be transmitted by the IMDs 10, 10', 10". In one embodiment, an interrogation session may be initiated by a clinician, a patient, or may be performed automatically according to a predetermined schedule. However, it should be noted that, in alternative embodiments, other methods of initiating an interrogation may be used without departing from the scope of the present invention.

If the remote monitor detects (at 366) at least one IMD 10, 10', 10", then the IMD 10, 10', 10" may, in one embodiment, transmit (at 368) an identification number that may be used to uniquely identify the IMD 10, 10', 10". The remote monitor 290 may receive and store (at 368) the identification number. For example, in one embodiment, individual IMDs 10, 10', 10" may be given a unique serial number that may be stored electronically in the IMD 10, 10', 10" and may be transmitted to the remote monitor 290. Using the identification number, the remote monitor 290 may then check (at 370) the request queue on the server 285 to determine (at 372) whether or not there are any programming requests pending for the IMD 10, 10', 10". If no requests are pending, the remote monitor 290 may end (at 380) the interrogation session.

Referring to FIG. 10C, a flow chart illustrating a method by which pending requests may be retrieved (at 382) from the server 285 by the remote monitor 290 is shown. It may, in one embodiment, be desirable to place the pending requests in order from the substantially older requests to the more recent requests. Thus, the remote monitor 290 may approximately synchronize (at 390) an internal clock to a clock that may be located in the server 285. For example, in one embodiment, the server 285 may comprise a clock that approximately but with reasonable accuracy maintains Greenwich Mean Time. The server 285 may check (at 392) that the identification number of the IMD 10, 10', 10" substantially matches the request. If the identification number does not substantially match (at 394) the request, indicating that the pending requests may not be intended for the IMD 10, 10', 10", the server 285 may return (at 400) no pending requests to the remote monitor 290.

If the identification number matches (at 394), indicating that the pending requests are intended to be transmitted to the IMD 10, 10', 10", the server may send (at 412) the request to the remote monitor over the secure connection indicated by the line 295. The remote monitor 290 may then decrypt (at 414) the request. For example, in one embodiment, the request may be encrypted (at 410) using at least one of a VPN or an SSL connection. The remote monitor 290 may decrypt (at 414) the request using the VPN or SSL.

To reduce the chance that rogues or hackers may be able to transmit erroneous, and potentially life-threatening, requests to the remote monitor 290, the remote monitor 290 may re-check (at 416) the identification number that may be attached to the pending requests that may have been transmitted by the server 285. If the identification number does not substantially match (at 420) the request, indicating that the pending requests may not be intended for the IMD 10, 10', 10", the remote monitor 290 may return (at 400) an error notification to the server 285 and remove the pending requests. If the identification number does substantially match (at 420) the request, indicating that the pending requests may be intended for the IMD 10, 10', 10", the remote monitor 290 may then sort (at 422) the list of pending requests in approximate order of their submission time.

Referring back now to FIG. 10B, the remote monitor 290 may, in one embodiment, examine (at 430) a pending request that may remain in the list transmitted by the server 285. The remote monitor may read (at 430) a sequence number that may be stored on the IMD 10, 10', 10". The sequence number may, in one embodiment, be a number that the IMD 10, 10', 10" may assign, starting at zero and incrementing by one, to each successive programming instruction that may be received from the remote monitor 290. However, it should be noted that any other numbering scheme may be used without substantially changing the scope or the spirit of the present invention, as will be appreciated by those of ordinary skill in the art.

If the remote monitor 290 determines (at 432) that the sequence number attached to the pending request is substantially not one greater than the current sequence number stored on the IMD 10, 10', 10", then the remote monitor 290 may transmit (at 434) an error message to the server and end (at 380) the interrogation session. In alternative embodiments, the remote monitor 290 may further determine (at 432) whether any other desirable information, such as the identification number, is substantially correct. If the remote monitor 290 determines (at 432) that the sequence number attached to the pending request is one greater than the current sequence number stored on the IMD 10, 10', 10", then the remote monitor 290 may transmit (at 440) the request to the IMD 10, 10', 10", which may make any requested changes and then transmit an acknowledgement to the remote monitor 290. The remote monitor 290 may then check (at 444) whether any requests remain to be processed. If additional requests remain, then the remote monitor 290 may examine (at 430) the next request. If no additional requests remain, the remote monitor may transmit an acknowledgement to the server 285 and end (at 380) the interrogation session.

Although the steps described in FIGS. 10A–C have been described as occurring sequentially with no delay between the successive steps, it will be appreciated that the present invention is not so limited. In alternative embodiments, the steps described in FIGS. 10A–C may occur in any desirable order or substantially simultaneously. The steps described in FIGS. 10A–C may also, in one embodiment, occur after a delay. For example, in-clinic requests may be queued for less than one-half hour without interrupting the in-clinic programming session.

Thus, the remote programming system 280 may, in one embodiment, provide a secure method for creating, storing, and transmitting program requests to an IMD 10, 10', 10" that may not be physically proximate to the programmer 20. The various steps of the process, which may include, but are not limited to, creating, storing and transmitting the programming requests, may be performed at substantially different times. Consequently, the clinician may create and submit programming requests at their convenience and the IMD 10, 10', 10" may be programmed at a time and place that may be more convenient to the patient. Benign programming that poses little or no threat to the patient may also occur in locations that may not have immediate access to rescue equipment.

Accordingly, the present invention provides a plurality of cooperative and complementary software programs implemented in a web-enabled high speed computer system to remotely monitor, manage and modify the operational and functional parameters of a plurality of implanted medical devices in a patient on a real-time basis. A high speed wireless data communications scheme is used to promote data exchange and transfer between the remote data center 62 and the IMDs 10, 10' and 10". The IMDs 10, 10' and 10' may be accessed via the programmer 20 or the IMU 20' which may be locally placed to be within a telemetric communications range. The VEM 100, the CMM 102 and the PPM 104 may enable remote and continuous monitoring to identify a critical medical event, determine medical device setting and install prescriptive programs in a plurality of medical devices. The various software programs are integrated to provide a seamless real-time management of implanted medical devices to promote efficient and real-time clinical care and therapy remotely.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A system, comprising:
    a programmer for creating, at a first selected time, a plurality of requests to modify the behavior of at least one of a plurality of implantable medical devices that deliver therapies to at least one of a plurality of patients, wherein a clinician utilizes the programmer to create the requests;
    a secure bi-directional communication network;
    a server coupled to the bi-directional communication network at a first location and that receives, stores, and encrypts the requests, wherein the server also verifies that the clinician is authorized to submit requests to the at least one of the plurality of implantable medical devices; and
    a plurality of monitors coupled to the bi-directional communication network at a plurality of second selected locations remote from the programmer to receive and decrypt the requests from the server, establish programming telemetry sessions with implantable medical devices, which requests to modify the behavior of the implantable medical device have previously been received by the implantable medical device, and transmit any request not yet received by the at least one of the plurality of implantable medical devices to modify the behavior to the at least one of the plurality of implantable medical devices in an order created on the programmer.

2. The system of claim 1, wherein the bi-directional communications network comprises at least one of a telephone line, an intranet, an internet, a satellite, and a global positioning system.

3. The system of claim 1, wherein at least one of the plurality of second selected times is substantially later than the first selected time.

* * * * *